Figure 1:
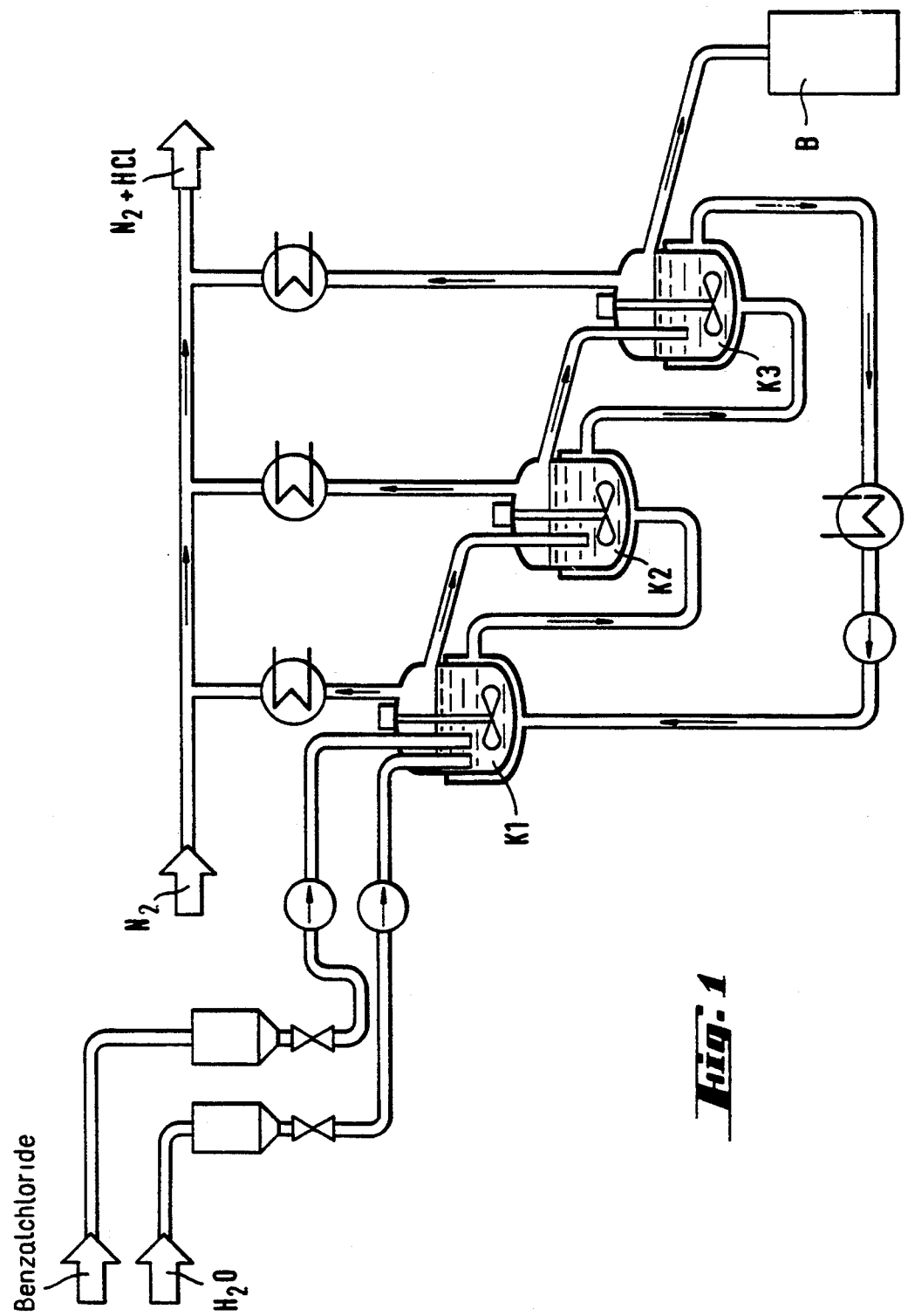

United States Patent [19]
Billeb et al.

[11] Patent Number: 5,382,694
[45] Date of Patent: Jan. 17, 1995

[54] PROCESS FOR THE CONTINUOUS PRODUCTION OF AROMATIC ALDEHYDES

[75] Inventors: Gilbert Billeb, Kelkheim/Taunus; Georg Folz, Frankfurt am Main, both of Germany

[73] Assignee: Hoechst Aktiengesellschaft, Frankfurt, Germany

[21] Appl. No.: 156,601

[22] Filed: Nov. 23, 1993

[30] Foreign Application Priority Data

Nov. 26, 1992 [DE] Germany ............................ 4239736

[51] Int. Cl.$^6$ ...................... C07C 45/43; C07C 45/42
[52] U.S. Cl. .................... 568/437; 568/426; 568/433
[58] Field of Search ................ 568/437, 433, 426

[56] References Cited

U.S. PATENT DOCUMENTS

| | | |
|---|---|---|
| 3,524,885 | 8/1970 | Deinet . |
| 3,624,157 | 11/1971 | Ingwalson . |
| 5,227,531 | 7/1993 | Mertz et al. . |

FOREIGN PATENT DOCUMENTS

| | | | |
|---|---|---|---|
| 2044832 | 3/1971 | Germany ............................ | 568/437 |
| 2044832 | 3/1971 | Germany ............................ | 568/437 |
| 2026817 | 12/1971 | Germany ............................ | 568/437 |
| 766 | 2/1963 | Japan ................................ | 568/437 |
| 0204736 | 10/1985 | Japan ................................ | 568/437 |
| 0218349 | 11/1985 | Japan ................................ | 568/437 |
| 0248640 | 12/1985 | Japan ................................ | 568/437 |
| 7215589 | 5/1973 | Netherlands ..................... | 568/437 |
| 1303376 | 1/1973 | United Kingdom ............ | 568/437 |
| 1307437 | 2/1973 | United Kingdom ............ | 568/437 |

OTHER PUBLICATIONS

Derwent Abstract of JP 60248640, Dec. 1985, Abstract No. 86–025603.
Derwent Abstract of JP 60218349, Nov. 1985, Abstract No. 85–313611.

*Primary Examiner*—Werren B. Lone
*Attorney, Agent, or Firm*—Connolly and Hutz

[57] ABSTRACT

A process for the continuous production of aromatic aldehydes of the formula (1)

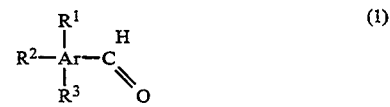

in which Ar is an aryl radical, $R^1$, $R^2$ and $R^3$ independently of one another are hydrogen, fluorine, chlorine or bromine atoms, in which dichloromethyl-substituted aromatics of the formula (2)

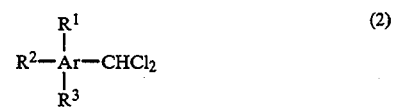

in which Ar, $R^1$, $R^2$, $R^3$ have the above meanings, are continuously hydrolyzed with an aqueous solution of one or more catalysts of the formula (3)

$$MX_n \qquad (3)$$

in which M is a transition metal selected from the group comprising iron, nickel, copper, chromium, thallium, zinc and mercury, X is F, Cl, Br, I, OH, $SO_4$, $PO_4$ or $NO_3$, and n depending on the oxidation state of the transition metal M is the number 1, 2, 3 or 4, in a concentration of from about 1 to about 50%, based on the weight of water in the catalyst solution, at temperatures of from about 70° to about 160° C.

18 Claims, 1 Drawing Sheet

PROCESS FOR THE CONTINUOUS PRODUCTION OF AROMATIC ALDEHYDES

The present invention relates to an improved process for the continuous production of halogenated aromatic aldehydes in very good yields by hydrolysis of the corresponding dichloromethyl-substituted aromatics with aqueous solutions of certain catalysts.

Aromatic aldehydes are important starting materials for the production of numerous compounds in the area of crop protection agents and pharmaceuticals.

Aromatic aldehydes are generally produced by saponification of the corresponding dichloromethyl-substituted aromatics with water in the presence of acids or metal salts in accordance with the reaction equation

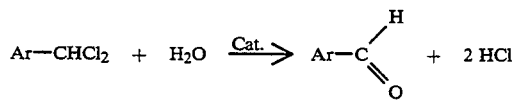

(cf. Houben-Weyl, VII, p.211 ff.), the reaction mostly being carried out batchwise. However, this mode of operation has the disadvantages below:

1. Reaction times are generally very long, which necessitates large equipment dimensions.
2. Larger production batches in particular are associated with an increased safety risk, since from time to time the start of saponification is delayed and the reaction can go out of control.
3. There are difficulties with the use of catalysts, such as iron salts, which can catalyze undesired side reactions (Friedel-Crafts reactions, polymerizations), because in the batch mode of operation at the beginning of the reaction there are high concentrations of dichloromethyl-substituted aromatic present, which favor such reactions. These reactions can often proceed in an uncontrolled way and finally lead to yield reduction or resinification of the batch.

There is therefore, for a number of reasons, a need for an improved process for producing substituted or unsubstituted aromatic aldehydes, which does not have the stated disadvantages.

In the literature there are already three continuous processes described for the production of benzaldehydes in accordance with the above reaction scheme:

In the Japanese disclosure 17217/62, Hodogaya Chemical Co., Ltd., the continuous saponification of various benzal chlorides in the presence of large amounts of sulfuric acid is presented. This process is still questionable from an ecological and economic point of view, since huge amounts of sulfuric acid are needed which finally enter the waste water or have to be regenerated at great expense. The conversion in this process is a maximum of 97%, which necessitates a great amount of distillation for separating off excess benzal chloride. Furthermore, it is very difficult to obtain a chlorine-free product in this way. The yield of aldehyde, based on the benzal chloride used, is very moderate at 87.5% of theoretical.

GB 2 103 208 describes a method for producing benzaldehydes in the gas phase. This method is only suitable for thermally stable aldehydes and is, both energetically and in respect of the active compounds (230° C., HCl waste gas), not unproblematical.

EP 64 486 describes a continuous process for producing benzaldehydes, wherein the saponification is carried out in an inert solvent with an aqueous solution of a base in a multistage counter-current extraction plant. Because of both the formation of waste waters with a high sodium chloride content and the necessity of large amounts of circulating solvents this process is ecologically problematical and expensive.

It has now been found that aromatic aldehydes of the formula (1)

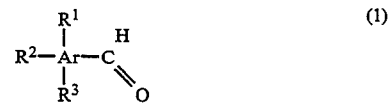

in which Ar is an aryl radical having from 6 to 14 carbon atoms, for example and preferably the benzene radical, $R^1$, $R^2$, $R^3$ independently of one another are hydrogen, fluorine, chlorine or bromine atoms, preferably hydrogen, fluorine or chlorine atoms, can advantageously be produced continuously by hydrolyzing dichloromethyl-substituted aromatics of the formula (2)

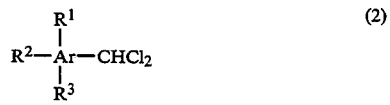

in which Ar, $R^1$, $R^2$, $R^3$ have the above meanings, with an aqueous solution of one or more catalysts of the formula (3)

$$MX_n \qquad (3)$$

in which M is a transition metal selected from the group comprising iron, nickel, copper, chromium, thallium, zinc and mercury, preferably from the group comprising iron, copper and zinc, particularly preferably from the group comprising iron and zinc, X is F, Cl, Br, I, OH, $SO_4$, $PO_4$ or $NO_3$, preferably Cl, Br, OH, $SO_4$, $PO_4$ or $NO_3$, and n depending on the oxidation state of the transition metal M is the number 1, 2, 3 or 4, in a concentration of from about 1 to about 50% by weight, preferably from about 1.2 to about 15% by weight, based on the weight of water in the catalyst solution, at temperatures of from about 70° to about 160° C., preferably from about 100° to about 140° C. in the presence of water required for hydrolysis in a stoichiometric amount up to an excess of about 100%, based on the compound of the formula (2).

The dichloromethyl-substituted aromatic of the stated formula (2) serving as starting compound can be used in pure form or mixed with the corresponding trichloromethyl-substituted aromatic, which makes possible the simultaneous production of aromatic aldehyde and aromatic carboxylic acid. If a mixture is used, this can contain up to about 50% by weight, for example from about 0.5 to about 30% by weight, of the corresponding trichloromethyl-substituted aromatic. Minor contamination of the starting compound of the formula (2) by the corresponding monochloromethyl-substituted aromatic does not interfere with the saponification reaction.

If a mixture of a dichloromethyl-substituted aromatic, for example benzal chloride, and a trichloromethyl-substituted aromatic, for example benzotrichloride, is used, then after completion of the reaction and before or after a distillation step the aromatic carboxylic acid formed can be extracted by an alkaline scrub and precipitated from the resulting solution by acidification and isolated.

In the process of the invention the yield of pure aldehyde, for example of halogenated or non-halogenated benzaldehyde, is >95%, based on the halogenated or nonhalogenated benzal chloride used. If a mixture of, for example, benzal chloride and benzotrichloride is used, the yield of carboxylic acid is >95% and the yield of aldehyde is >95% after separation and purification of the products.

The process of the invention is also particularly notable for small amounts of metal salts, based on starting material of the formula (2) used, being sufficient (from about 0.1 to about 1.5 g/100 g). In comparison, in the process of JP 17217/62 from about 40 to 50 g of concentrated sulfuric acid are needed per 100 g of starting compound. In addition, it is possible to safely use aqueous iron salt or, surprisingly, aqueous zinc salt solutions. Zinc salt solutions, unlike solid zinc salts, are not catalytically active in the batch process (J. Legocki et al., Pr. Inst. Przem. Org. 1974, 6, 1–9). It is therefore even more surprising that in the continuous mode of operation the saponification with, for example, 10 percent strength aqueous zinc chloride solution proceeds smoothly and with very high conversions and yields. The use of a solid zinc salt as catalyst would be very difficult to achieve in a continuous mode of operation because of metering problems.

A preferred embodiment of the process of the invention therefore also comprises carrying out the saponification of the compounds of the stated formula (2) with an aqueous solution of iron or zinc salts of the above-named anions as catalysts.

It is advantageous to carry out the process of the invention, i.e. the hydrolysis of the compounds of the stated formula (2), in a cascade of stirred reactors comprising from 2 to 5, preferably from 2to 3, heatable stirred reactors connected in series, in which case the dichloromethyl-substituted aromatic of the formula (2), for example benzal chloride, in pure (or contaminated by small amounts of monochloromethyl-substituted aromatic, for example benzyl chloride) form or if required a mixture of dichloromethyl-substituted aromatic, for example benzal chloride, and the corresponding trichloromethyl-substituted aromatic, for example benzotrichloride, and the aqueous catalyst solution are metered into the first reactor and the resulting reaction mixture is allowed to pass by means of overflows or pumps into the downstream reactors. In the downstream reactors, water or aqueous catalyst solution can be additionally metered in as needed.

The water required for hydrolysis is used in the stoichiometric amount or in an excess of up to about 100%, preferably up to about 15%, based on the starting compound of the stated formula (2).

The reaction temperature in all reactors is from about 70 to about 160° C., preferably from about 100 to about 140° C. The average residence time in each vessel is from about 30 to about 240 minutes, preferably from about 40 to about 80 minutes, the residence time in the individual reactors also being able to be different.

The reaction is preferably carried out in such a way that the conversion in the first reactor is already >85%, preferably >90%.

The crude product exiting the final reactor of the cascade has a content of dichloromethyl-substituted aromatic, for example benzal chloride, of less than 1%, preferably less than 0.1%, and of aromatic aldehyde, for example benzaldehyde, without considering excess water, of >99%. The material can after dewatering be distilled or processed further in the crude state.

The examples below serve to illustrate the process without limiting it to them.

Preface to the examples:

A BRIEF DESCRIPTION OF THE DRAWING

All the examples below were carried out in a cascade of stirred reactors, comprising three heatable stirred reactors K1 to K3 connected in series, as in the accompanying diagram (cf. FIG. 1). Before each actual experiment the cascade was filled with aromatic aldehyde of the stated formula (1) or with prepared reaction mixture and brought to reaction temperature. (In FIG. 1, B is the product receiver.)

EXAMPLE 1

(saponification of o-chlorobenzal chloride)

The reactors K1 to K3 were filled to the overflow with a batchwise-produced reaction mixture having an o-chlorobenzaldehyde content of about 98% and were heated to 130° C. Subsequently, o-chlorobenzal chloride at a metering rate of 268 ml/h (369.8 g, 1.89 mol) and 10% strength zinc chloride solution at a metering rate of 36 ml/h were metered into the reactor K1. The volume flow leaving the cascade was 220 ml/h and the average residence time in each reactor was about 60 minutes. After 5 hours the cascade was in equilibrium. The conversion in reactor K1 was 99.3%. The crude product leaving the cascade at equilibrium had an o-chlorobenzal chloride content of <0.04% (capillary GC percentage area) and without considering excess water was 99.5% strength in o-chlorobenzaldehyde. The yield of pure o-chlorobenzaldehyde was about 256 g/h (1.82 mol/h, 96% of theoretical).

EXAMPLE 2

(saponification of o-chlorobenzal chloride)

As a change to Example 1, the residence time was shortened to 47 minutes per reactor by increasing the material flows. The cascade was initially filled with prepared reaction mixture as in Example 1. o-Chlorobenzal chloride at a metering rate of 356 ml/h (491 g/h, 2.5 mol/h) and 10% strength zinc chloride solution at a metering rate of 43.6 ml/h were metered into reactor K1. Additionally, 10% strength zinc chloride solution at a metering rate of 3.6 ml/h was metered into reactor K2. After 3 hours the cascade was in equilibrium (GC monitoring). The material flow leaving the system was 294 ml/h. At equilibrium, the o-chlorobenzal chloride content in reactor K1 was about 6%, in reactor K2 about 0.7% and in reactor K3 and in the stream leaving the system was about 0.05% (all data capillary GC percentage areas). The o-chlorobenzaldehyde content in the stream leaving the system was 99.7% (GC) without considering excess water. The yield of pure o-chlorobenzaldehyde was 280 ml/h (339 g/h, 2.41 mol/h, 96% of theoretical).

EXAMPLE 3

( saponification of p-chlorobenzal chloride )

The saponification of p-chlorobenzal chloride was carried out in accordance with Example 1 at a reaction temperature of 100° C. with the same material flows and residence times. At equilibrium, the conversion of p-chlorobenzal chloride in reactor K1 of the cascade was about 98% and was quantitative in reactor K2. The crude product had a p-chlorobenzaldehyde content of >99%. The yield of pure p-chlorobenzaldehyde was 255 g/h (96% of theoretical).

EXAMPLE 4

(saponification of a mixture of o-chlorobenzotrichloride and o-chlorobenzal chloride )

The saponification was carried out analogously to Example 1 with a mixture of 76.1% by weight of o-chlorobenzotrichloride chloride and 23.5% by weight of o-chlorobenzotrichloride at the same temperature and the same volume flows. No significant differences in the saponification rate were found. The o-chlorobenzotrichloride is completely saponified under the reaction conditions to o-chlorobenzoic acid. Continuous scrubbing of the saponification mixture with 4% strength sodium carbonate solution extracted the o-chlorobenzoic acid, and the crude o-chlorobenzaldehyde was separated off in a phase separator and purified by distillation at 10 torr. The alkaline sodium carbonate solution was acidified with 30% strength hydrochloric acid, the o-chlorobenzoic acid being precipitated and filtered off. The yield of o-chlorobenzaldehyde was 95.1% of theoretical, based on o-chlorobenzal chloride used; that of the o-chlorobenzoic acid was 99% of theoretical, based on o-chlorobenzotrichloride used.

EXAMPLE 5

The saponification of o-chlorobenzal chloride was carried out under the same conditions as in Example 1 using 10% strength iron(II) sulfate solution. The same results as in Example 1 were obtained.

EXAMPLE 6

The saponification of o-chlorobenzal chloride was carried out analogously to Example 1 using 2% strength zinc chloride solution. No significantly different results were obtained.

EXAMPLE 7

The saponification of o-chlorobenzal chloride was carried out analogously to Example 1 using 10% strength Zn(OH)$_2$ solution. No differences were found from the use of zinc chloride.

EXAMPLE 8

The saponification of 2-chloro-6-fluorobenzal chloride was carried out at 140° C. analogously to Example 1. The input flow of 2-chloro-6-fluorobenzal chloride was 268 mg/h (396.6 g/h, 1.86 mol/h). The 10% strength zinc chloride solution was metered in at a metering rate of 6 ml/h. The volume flow leaving the cascade was 242 ml/h and the average residence time in each reactor was about 66 minutes. The crude product leaving the system had a 2-chloro-6-fluorobenzaldehyde content of 99.4%. The yield of pure 2-chloro-6-fluorobenzaldehyde was 280 g/h (1.77 mol, 95% of theoretical).

EXAMPLE 9

The saponification of 4-fluorobenzal chloride was carried out at 100° C. analogously to Example 1. The input volume flow of 4-fluorobenzal chloride was 268 ml/h (359 g/h, 2.0 mol/h). The volume flow leaving the system was 213 ml/h and was >99% strength in 4-fluorobenzaldehyde. The yield of pure 4-fluorobenzaldehyde was 235 g/h (94.7% of theoretical).

What is claimed is:

1. A process for the continuous production of aromatic aldehydes of the formula (1)

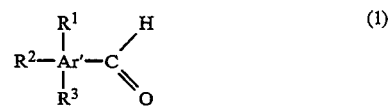
(1)

in which Ar' is an aryl radical having from 6 to 14 carbon atoms, R$^1$, R$^2$ and R$^3$ independently of one another are hydrogen, fluorine, chlorine or bromine atoms, which comprises continuously hydrolyzing a dichloromethyl-substituted aromatic starting compound of the formula (2)

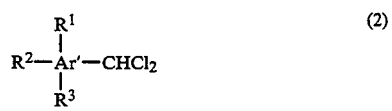
(2)

in which Ar', R$^1$, R$^2$, R$^3$ have the above meanings, with an aqueous solution of at least one catalyst of the formula (3)

$$MX_n \qquad (3)$$

in which M is a transition metal selected from the group comprising nickel, copper, and zinc, X is F, Cl, Br, I, OH, SO$_4$, PO$_4$ or NO$_3$, and n depending on the oxidation state of the transition metal M is the number 1, 2, 3 or 4, in a concentration of from about 1 to about 50%, based on the weight of water in the catalyst solution, at temperature of from about 70° to about 160° C.

2. The process as claimed in claim 1, wherein Ar' in the formulae (1) and (2) is the radical of benzene, naphthalene, anthracene or phenanthrene.

3. The process as claimed in claim 1, wherein Ar' in formulae (1) and (2) is the radical of benzene.

4. The process as claimed in claim 1, wherein hydrolysis is performed continuously with aqueous solutions of catalysts of the formula (3) given in claim 1, in which M is zinc.

5. The process as claimed in claim 1, wherein hydrolysis is performed continuously with aqueous solutions of zinc chloride as catalyst.

6. The process as claimed in at least one of claim 1, wherein hydrolysis is performed continuously at temperatures of from about 100° to about 140° C.

7. The process as claimed in claim 1, wherein the concentration of the aqueous solution of the catalyst is from about 1.2 to about 15%.

8. The process as claimed in claim 1, wherein the water required for hydrolysis is used in the stoichiometric amount or in an excess of up to about 100%, based on the equivalents of chlorine to be hydrolyzed in the starting compound of the formula (2) given in claim 1.

9. The process as claimed in claim 1, wherein the water required for hydrolysis is used in an excess of up to about 15% above the stoichiometric amount, based on the equivalents of chlorine to be hydrolyzed in the starting compound of the formula (2) given in claim 1.

10. The process as claimed in claim 1, wherein the continuous hydrolysis is carried out in a cascade of stirred reactors comprising from 2 to 5 heatable stirred reactors connected in series.

11. The process as claimed in claim 1, wherein the continuous hydrolysis is carried out in a cascade of stirred reactors comprising from 2 to 3 heatable stirred reactors connected in series.

12. The process as claimed in claim 10, wherein the dichloromethyl-substituted aromatic and the aqueous catalyst solution are continuously metered into the first reactor of the cascade and water or aqueous catalyst solution is additionally metered into the further reactors as needed.

13. The process as claimed in claim 10, wherein the residence time in the individual reactors, which can be the same or different in each said reactor, is from about 30 to about 240 minutes.

14. The process as claimed in claim 13, wherein the residence time in the individual reactors is from about 40 to about 80 minutes.

15. The process as claimed in claim 1, wherein an aromatic starting compound of said formula (2) is mixed with up to about 50% by weight of a corresponding trichloromethyl-substituted aromatic starting compound, and the continuous hydrolyzing step is carried out on the mixture.

16. The process as claimed in claim 15, wherein the amount of a said corresponding trichloromethyl substituted aromatic starting compound mixed with an aromatic starting compound of said formula (2) is about 0.5 to about 30% by weight.

17. The process as claimed in claim 1, which includes the step of facilitating the recovery of an aromatic aldehyde of said formula (1), before or after a distillative purification of the aromatic aldehyde, by separating off from the hydrolysis reaction mixture or from the distillation residue of said distillative purification an aromatic carboxylic acid formed in said hydrolysis reaction mixture.

18. The process as claimed in claim 17, wherein said recovering step is carried out by continuous alkali scrubbing of said hydrolysis reaction mixture or said distillation residue, and said aromatic carboxylic acid thereby separated off is precipitated in substantially pure form by acidification.

* * * * *